(12) United States Patent
Iyer et al.

(10) Patent No.: US 6,551,615 B1
(45) Date of Patent: Apr. 22, 2003

(54) DEXIBUPROFEN-CONTAINING SOFT GELATIN CAPSULES AND PROCESS FOR PREPARING THE SAME

(75) Inventors: V. S. Iyer, Bangalore (IN); Shivaraj B. Katageri, Bangalore (IN)

(73) Assignee: M/s. Strides Arcolab Limited, Mumbai ( * ) Notice: Subject to any disclaimer, the term of this patent is extended or adjusted under 35 U.S.C. 154(b) by 0 days.

(21) Appl. No.: 10/046,565

(22) Filed: Oct. 18, 2001

(51) Int. Cl.$^7$ .............................. A61K 9/48; A61K 9/64; A61K 47/32; A01N 25/00
(52) U.S. Cl. .................... 424/456; 424/451; 514/772.5; 514/886
(58) Field of Search ................................ 424/451, 456; 514/772.5, 886

(56) References Cited

U.S. PATENT DOCUMENTS

| | | | |
|---|---|---|---|
| 4,690,823 A | * | 9/1987 | Lohner et al. |
| 4,877,620 A | | 10/1989 | Loew et al. |
| 5,071,643 A | | 12/1991 | Yu et al. |
| 5,093,133 A | * | 3/1992 | Wisniewski et al. |
| 5,622,990 A | | 4/1997 | Katdare et al. |
| 5,869,102 A | | 2/1999 | Stroppolo et al. |
| 5,969,102 A | * | 10/1999 | Bram et al. |
| 5,976,566 A | | 11/1999 | Samour et al. |
| 6,005,005 A | | 12/1999 | Stroppolo et al. |
| 6,221,391 B1 | * | 4/2001 | Rouffer |
| 6,251,426 B1 | * | 6/2001 | Gullapalli |
| 6,255,347 B1 | * | 7/2001 | Xiaotao |

FOREIGN PATENT DOCUMENTS

| | | |
|---|---|---|
| EP | 0439344 A2 | 1/1991 |
| EP | 0753296 A2 | 1/1997 |

OTHER PUBLICATIONS

Evaluation of efficacy and dose response relationship of Dexlbuprofen with Osteoarthritis of the hip, etc., Index by F. Singer, Mayrhofer, etc.—International Journal of Clinical Pharmacology and Therapeutics, vol. 38—No. 1 (2000); pp. 25–29.

Physician's Desk Reference (1999, 53$^{rd}$ Edition) Product Information—Ibuprofen tablets; pp. 1667, 1676, 1678.

Martindale (32$^{nd}$ Edition)—The Complete Drug Reference by Kathleen Parfitt; pp. 44–45.

Transcutol—Product profile supplied by Ms. Gattefosse; pp. 1–9.

European Pharmacopoela (1998, corrected 2001); Monographs on Caprylocaproyl Macrogolglycerides; pp. 1184.

Labrasol—Product profile supplied by Ms. Gattefosse; specification No. 3074/02; Last update; Nov. 21, 2000.

Polyethylene Glycol 400–13 Handbook of Pharmaceutical excipients 2$^{nd}$ Edition by Ainley Wade and Paul J. Weller (1994); pp. 355–361.

Povidone (PVP K–30)—Handbook of Pharmaceutical excipients 2$^{nd}$ Edition by Ainley Wade and Paul J. Weller (1994); pp. 392–401.

Handbook of Pharmaceutical Excipients (2$^{nd}$ Edition) by Ainley Wade and Paul J. Weller (1994); pp. 371–374.

* cited by examiner

*Primary Examiner*—Thurman K. Page
*Assistant Examiner*—Humera N. Sheikh
(74) *Attorney, Agent, or Firm*—Knobbe, Martens, Olson & Bear, LLP

(57) ABSTRACT

The present invention relates to a formulation and process for preparing dexibuprofen soft gelatin capsules comprising dexibuprofen dissolved in diethylene glycol monoethylether. The dexibuprofen-containing soft gelatin capsule includes a substantially clear solution of about 40% by weight of dexibuprofen, about 40% by weight of a solubilizer, about 0.8% to 5% be weight of surfactants, about 14% to 20% by weight of co-surfactants, about 2% by weight of a potassium salt generating species, and about 2% by weight of a viscosity imparter.

8 Claims, No Drawings

DEXIBUPROFEN-CONTAINING SOFT GELATIN CAPSULES AND PROCESS FOR PREPARING THE SAME

BACKGROUND OF THE INVENTION

1. Field of the Invention

This invention generally relates to orally administrable pharmaceutical compositions and more particularly to dexibuprofen-containing soft gelatin capsules.

2. Description of the Related Art

The insolubility of solid drug forms in common media such as water poses a major challenge because of the resulting low bioavailability of the active ingredients. Liquid dosage forms, in contrast, generally have better bioavailability. One such liquid form is the soft gelatin, or softgel, capsule. Patient compliance is with softgel formulations is improved because soft gelatin capsules' soft, elastic character make them easier swallow than conventional tablets or hard gelatin capsules. Furthermore, since the dosage form is generally swallowed, it is unnecessary to flavor or otherwise mask any unpleasant taste of the active pharmaceutical ingredients. Finally unlike tablets, soft gelatin capsules do not chip or powder.

Another drug delivery issue is content uniformity. If a formulation is a true solution, content uniformity can be achieved. The active ingredient may be completely dissolved in a softgel formulation.

Dexibuprofen is a non-steroidal anti-inflammatory (NSAID), analgesic (pain relieving), and antipyretic (fever reducing) drug. NSAID is a general term for a specific group of drugs, which effectively reduce inflammation and pain. NSAIDs inhibit the body's production of prostaglandins and other compounds—such as cyclooxygenase, lipoxygenase, leukotrienes, and lysosomal enzymes—that sensitize pain receptors and stimulate inflammatory responses. NSAIDs are generally absorbed into the bloodstream. Pain and fever relief usually occurs within 1 hour of taking the first dose and can last up to 6 hours. The anti-inflammatory effect of these agents generally takes longer to work (several days to 2 weeks) and may take a month or more to reach maximum effect (*Physician's Desk Reference*, 53rd ed., 1667–76 (1999)).

Dexibuprofen is also known as (S)-(+)-2-(4-isobutylphenyl)propionic acid or (S)-ibuprofen. It is practically insoluble in water, but is freely soluble in methanol, methylene chloride, and acetone. Dexibuprofen is readily soluble in most organic solvents and is soluble in aqueous solutions of alkali hydroxides and-carbonates (Martindale, 32nd ed., K. Parfitt ed., 44).

Dexibuprofen is an effective non-steroidal, anti-inflammatory drug with a significant dose response relationship in patients with painful osteoarthritis of the hip. Compared with racemic ibuprofen, half of the daily dose of dexibuprofen shows at least equivalent efficacy (F. Singer, et al., *Int. J. Clin. Pharm. Ther.*, 38(J), 25–29 (2000)). Dexibuprofen is practically water insoluble, however, raising the issue of bioavailability.

Ibuprofen containing soft gelatin capsules are known. U.S. Pat. No. 4,690,823 to Lohner et al. describes soft gelatin capsules containing, by weight, a solution of 15 to 30 parts of ibuprofen in 70 to 85 parts of polyoxyethylene-polyoxypropylene polymer, or a mixture of 30 to 76 parts of polyalkylene glycol and 7 to 40 parts of a surfactant. These softgels exhibit very rapid and high bioavailability of the active ingredient. The active ingredient is not reprecipitated by aqueous media such as artificial gastric juice.

Gelatin-sheath-enclosed liquid softgel formulations containing ibuprofen as the free acid are described in U.S. Pat. No. 6,251,426 to Gullapalli. The softgels are prepared by dissolving greater than 30% by weight of ibuprofen free acid in polyethylene glycol and at least 10% of polyvinylpyrrolidone of an average molecular weight of about 2,000 to 54,000. These formulations may also include a surfactant to increase the bioavailability of the ibuprofen.

U.S. Pat. No. 6,255,347 to Xiaotao et al. describes the use of the R-enantiomer of ibuprofen, previously thought inactive. Particularly, Xiaotao et al. discloses that (R)-ibuprofen, is an antineoplastic agent, and also a prophylactic and therapeutic treatment of Alzheimer's and Alzheimer's related diseases.

European Patent Application EP0439344 describes an ibuprofen-containing, topical, hydroalcoholic gel for treating inflammation or pain. Corresponding U.S. Pat. No. 5,093,133 describes an ibuprofen-containing, topical, hydroalcoholic gel for treating inflammation or pain, methods for delivering ibuprofen through the skin to treat inflammation or pain using this gel; and using (S)-ibuprofen topically to treat inflammation or pain.

U.S. Pat. No. 5,869,102 describes a solid pharmaceutical composition containing (S)-ibuprofen as the active ingredient. These compositions are suitable for the preparation of tablets, sachets and capsules. The tablets contain (S)-ibuprofen, colloidal silica, microcrystalline cellulose, and magnesium stearate. Tablets are prepared by direct compression of the pharmaceutical composition and may be coated or filmed according to conventional techniques.

SUMMARY OF THE INVENTION

Accordingly, we sought to devise a soft gelatin capsule formulation of dexibuprofen. Because the dexibuprofen in this formulation is predissolved in the softgel, it may be more bioavailable compared to solid dexibuprofen.

In accordance with one preferred embodiment, there are provided formulations of substantially clear solutions of dexibuprofen. More specifically, preferred pharmaceutical formulations disclosed herein comprise a substantially clear dexibuprofen solution containing about 40% by weight of dexibuprofen, about 40% by weight of a solubilizer, about 0.8% to 5% by weight of surfactants, about 14% to 20% by weight of co-surfactants, about 2% by weight of a potassium salt generating species, and about 2% by weight of a viscosity imparter.

In accordance with another preferred embodiment, there are provided soft gelatin capsules of dexibuprofen made from a pharmaceutical formulation comprising a substantially clear dexibuprofen solution containing about 40% by weight of dexibuprofen, about 40% by weight of a solubilizer, about 0.8% to 5% by weight of surfactants, about 14% to 20% by weight of co-surfactants, about 2% by weight of a potassium salt generating species, and about 2% by weight of a viscosity imparter.

In accordance with yet another preferred embodiment, there are provided methods of making these dexibuprofen-containing soft gelatin capsules, which comprise a substantially clear dexibuprofen solution containing about 40% by weight of dexibuprofen, about 40% by weight of a solubilizer, about 0.8% to 5% by weight of surfactants, about 14% to 20% by weight of co-surfactants, about 2% by weight of a potassium salt generating species, and about 2% by weight of a viscosity imparter.

A preferred solubilizer is diethylene glycol monoethyl ether. Preferred surfactants are caprylocaproyl macrogolglycerides or polyoxyethylene castor oil derivatives. Particularly preferred polyoxyethylene castor oil derivatives are polyoxyl(40) hydrogenated castor oil or polyoxyl(35) hydrogenated castor oil. A preferred co-surfactant is polyethylene glycol 400. A preferred potassium salt generating species is potassium hydroxide. A preferred viscosity imparter is polyvinylpyrrolidone. A particularly preferred viscosity imparter is povidone (PVP K-30).

One advantage of preferred embodiments is that the high solubility of dexibuprofen in diethyleneglycol monoethylether allows the production of softgels of acceptable sizes. In the present invention the dexibuprofen in the softgel is present as both the potassium salt and the free acid.

DETAILED DESCRIPTION OF THE PREFERRED EMBODIMENT

The present invention relates to dexibuprofen solutions in soft gelatin capsules. We conducted solubility studies on various solvents including polyethylene glycol, propylene glycol, alcohol, and diethylene glycol monoethyl ether. We discovered that dexibuprofen dissolved in diethylene glycol monoethyl ether (Transcutol® P, Gattefossé) in a better than 1:1 ratio without heating.

Preferred formulations use diethyleneglycol monoethylether, a powerful solubilizing agent, to dissolve the dexibuprofen. Highly purified diethyleneglycol monoethylether is commercially available as Transcutol® P (Gattefossé). Diethyleneglycol monoethylether solubilizes drugs that are commonly thought to be insoluble or difficult to solubilize (European Pharmacopoeia). It is soluble in water, ethanol, hexylene glycol, and propylene glycol, and is partially soluble in vegetable oils (Transcutol Product Profile, Gattefossé, 1–9).

Preferred formulations contain caprylocaproyl macrogolglycerides (Labrasol®, Gattefossé), which is a mixture of mono-, di-, and triglycerides, and mono- and diesters of macrogols with a mean molecular weight of about 200 to 400 (*British Pharmacopoeia; European Pharmacopoeia*, 1184 (1998, corrected 2001)). The caprylocaproyl macrogolglycerides act as surfactants, emulsifying the formulation when exposed to aqueous media thereby enhancing the bioavailability of dexibuprofen.

Polyoxyl(40) hydrogenated castor oil or polyoxyl(35) hydrogenated castor oil may be used as surfactants in place of caprylocaproyl macrogolglycerides. These compounds are commercially available as Cremophor RH 40 and Cremophore RH 35 (BASF). Polyoxyethylene castor oil derivatives are complex mixtures of various hydrophobic and hydrophilic components. About 75% of the components are hydrophobic, and are composed mainly of fatty acid esters of glycerol polyethylene glycols, and fatty acid esters of polyethylene glycol. The hydrophilic portion consists of polyethylene glycol and glycerol ethoxylates. Polyoxyl(40) hydrogenated castor oil is a slightly opalescent liquid, whereas polyoxyl(35) hydrogenated castor oil is a clear liquid. Polyoxyl(40) hydrogenated castor oil has an HLB value of 11 to 14 (A. Wade, P.J. Weller, *Handbook of Pharmaceutical Excipients*, 2nd ed., 371 (1994)).

We have found polyethylene glycol 400 useful in the formulation as cosurfactant to aid the emulsification. Polyethylene glycols have been used to enhance the aqueous solubility or dissolution characteristics of poorly soluble drugs (A. Wade, P.J. Weller, *Handbook of Pharmaceutical Excipients*, 2nd ed., 355–61, (1994)).

The softgel formulation preferably also contains polyvinylpyrrolidone (povidone, PVP). Povidone (PVP K-30) has been used in a variety of pharmaceutical formulations. Polyvinylpyrrolidone with molecular weight of from about 2500 to 50,000 is preferred. Povidone is known to prevent dexibuprofen from precipitating (A. Wade, P. J. Weller, *Handbook of Pharmaceutical Excipients*, 2nd ed., 392401 (1994)). It also imparts viscosity to the solution, which aids in filling the drug delivery device, in this case a soft gelatin capsule.

One preferred embodiment discloses soft gelatin capsules in which the dexibuprofen is present as both the potassium salt and the free acid. Potassium hydroxide was used to convert dexibuprofen into its potassium salt. Because salts of acids are known to dissolve better in aqueous solution than the corresponding free acid, using the salt should improve the bioavailability of the dexibuprofen. Those skilled in the art will recognize that other compounds, for example potassium carbonate or potassium bicarbonate, could be used to generate the potassium salt of dexibuprofen. Also, cations other than potassium, including other monovalent cations, divalent and polyvalent cations, or organic cations, are within the scope of the present invention.

Preferred embodiments are further illustrated in the following examples.

EXAMPLES

Example 1

| | Dexibuprofen dose per soft gel capsule | | | |
|---|---|---|---|---|
| Ingredient | 150 mg | 200 mg | 300 mg | 450 mg |
| Dexibuprofen IH | 150 mg | 200 mg | 300 mg | 450 mg |
| Diethyleneglycol monoethylether (Transcutol P) EP | 150 mg | 200.0 mg | 300.0 mg | 450 mg |
| Caprylocaproyl macrogolglycerides (Labrasol) BP | 3.0 mg | 4.0 mg | 6.0 mg | 9.0 mg |
| Polyethylene glycol 400 BP | 57.0 mg | 76.0 mg | 114.0 mg | 171.0 mg |
| Potassium hydroxide BP | 7.5 mg | 10.0 mg | 15.0 mg | 22.5 mg |
| Povidone (PVP K-30) BP | 7.5 mg | 10.0 mg | 15.0 mg | 22.5 mg |
| Fill weight per capsule | 375.0 mg | 500.0 mg | 750.00 mg | 1125.0 mg |
| Capsule size | 6 minim Oblong | 8 minim Oblong | 8 minim Oblong | 14 minim Oblong |

Example 2

| | Dexibuprofen dose per soft gel capsule | | | |
|---|---|---|---|---|
| Ingredient | 150 mg | 200 mg | 300 mg | 450 mg |
| Dexibuprofen IH | 150 mg | 200 mg | 300 mg | 450 mg |
| Diethyleneglycol monoethylether (Transcutol P) EP | 150 mg | 200.0 mg | 300.0 mg | 450 mg |
| Polyoxyl(40) hydrogenated castor oil USP | 9.0 mg | 12.0 mg | 18.0 mg | 27.0 mg |

-continued

Dexibuprofen dose per soft gel capsule

| Ingredient | 150 mg | 200 mg | 300 mg | 450 mg |
|---|---|---|---|---|
| Polyethylene glycol 400 BP | 51.0 mg | 68.0 mg | 102.0 mg | 153.0 mg |
| Potassium hydroxide BP | 7.5 mg | 10.0 mg | 15.0 mg | 22.5 mg |
| Povidone (PVP K-30) BP | 7.5 mg | 10.0 mg | 15.0 mg | 22.5 mg |
| Fill weight per capsule | 375.0 mg | 500.0 mg | 750.00 mg | 1125.0 mg |
| Capsule size | 6 minim Oblong | 8 minim Oblong | 8 minim Oblong | 14 minim Oblong |

Example 3

Dexibuprofen dose per soft gel capsule

| Ingredient | 150 mg | 200 mg | 300 mg | 450 mg |
|---|---|---|---|---|
| Dexibuprofen IH | 150 mg | 200 mg | 300 mg | 450 mg |
| Diethyleneglycol monoethylether (Transcutol P) EP | 150 mg | 200.0 mg | 300.0 mg | 450 mg |
| Polyoxyl(35) hydrogenated castor oil USP | 9.0 mg | 12.0 mg | 18.0 mg | 27.0 mg |
| Polyethylene glycol 400 BP | 51.0 mg | 68.0 mg | 102.0 mg | 153.0 mg |
| Potassium hydroxide BP | 7.5 mg | 10.0 mg | 15.0 mg | 22.5 mg |
| Povidone (PVP K-30) BP | 7.5 mg | 10.0 mg | 15.0 mg | 22.5 mg |
| Fill weight per capsule | 375.0 mg | 500.0 mg | 750.00 mg | 1125.0 mg |
| Capsule size | 6 minim Oblong | 8 minim Oblong | 8 minim Oblong | 14 minim Oblong |

In general, gelatin capsule formulations for soft gelatin capsules comprise raw gelatin and one or more plasticizers added to adjust the hardness of the capsule. Typical plasticizers include glycerin, sorbitol and Anidrisorb 85/70. A preferred plasticizer is Anidrisorb 85/70, an aqueous solution of D-sorbitol and sorbitans. In some instances, we found that glycerin reacts with dexibuprofen forming unwanted glycerol esters of dexibuprofen. One preferred gelatin formulation for the soft gelatin capsules used in accordance with preferred embodiments includes gelatin in the range of about 40% to 48% and a plasticizer ranging in amount from about 20% to 35%. Another preferred plasticizer is sorbitol BP, a non-crystallizing sorbitol solution. When either a 70%, non-crystallizing sorbitol solution or Anidrisorb 85/70 are used alone, the amount of plasticizer used preferaby ranges from about 25% to 35%. Capsule formulations can also include other suitable additives, for example coloring agents, which impart specific characteristics such as the look and feel of the capsule. FD&C dyes and D & C dyes are examples of pharmaceutically acceptable coloring agents that may be used in preferred embodiments.

The following examples illustrate preferred embodiments of several soft-gelatin-shell dexibuprofen formulations. These examples illustrate particular embodiments of the invention and are not intended to limit the scope of the invention in any way.

Example 4

| Ingredient | Percentage by weight |
|---|---|
| Gelatin | 44.5 |
| Sorbitol Solution, 70% (non-crystallizable) | 9.3 |
| Glycerin | 14.0 |
| Purified water | 32.2 |

Example 5

| Ingredient | Percentage by weight |
|---|---|
| Gelatin | 44.5 |
| Glycerin | 14.00 |
| Sorbitol Solution, 70% (non-crystallizable) | 9.30 |
| Purified water | 32.20 |

Example 6

| Ingredient | Percentage by weight |
|---|---|
| Gelatin | 44.5 |
| Glycerin | 14.00 |
| Sorbitol and sorbitan esters (Anidrisorb85/70) | 9.30 |
| Purified water | 32.20 |

Example 7

| Ingredient | Percentage by weight |
|---|---|
| Gelatin | 44.5 |
| Sorbitol solution, 70% (non-crystallizable) | 25.00 |
| Purified water | 30.50 |

Example 8

| Ingredient | Percentage by weight |
|---|---|
| Gelatin | 44.5 |
| Sorbitol and sorbitan esters (Anidrisorb85/70) | 25.00 |
| Purified water | 33.00 |

The dissolution profiles of dexibuprofen soft gelatin capsules made according to Examples 1 and 8, encapsulated in 8 minim oblong soft gelatin capsules were determined using USP dissolution apparatus #2 at 37° C. in three media: pH 7.5 phosphate buffer, pH 6.5 phosphate buffer, and water. The stirring paddle was set at 50 RPM for 1 hour; the release of dexibuprofen was monitored by UV at 264 nm. The results are shown in Table I.

TABLE I

| | Percentage of dexibuprofen released | | |
|---|---|---|---|
| Time | Water | pH 6.5 phosphate buffer | pH 7.5 phosphate buffer |
| 20 min | 77.23% | 93.28% | 90.0% |
| 40 min | 83.82% | 95.58% | 95.2% |
| 60 min | 87.85% | 96.27% | 101.5% |

Certain modifications and improvements of the disclosed invention will occur to those skilled in the art without departing from the scope of invention, which is limited only by the appended claims.

What is claimed is:

1. A pharmaceutical formulation comprising:
    a substantially clear solution in a soft gelatin capsule, wherein the solution comprises:
        about 40% by weight of dexibuprofen;
        about 40% by weight of a solubilizer;
        about 0.8% to 5% by weight of surfactants;
        about 14% to 20% by weight of co-surfactants;
        about 2% by weight of a potassium salt generating species; and
        about 2% by weight of a viscosity imparter.

2. The pharmaceutical formulation according to claim 1 wherein the solubilizer is diethylene glycol monoethyl ether.

3. The pharmaceutical formulation according to claim 1 wherein the surfactant is a caprylocaproyl macrogolglyceride with a mean relative molecular weight of between about 200 and 400.

4. The pharmaceutical formulation according to claim 1 wherein the viscosity imparter is polyvinylpyrrolidone with molecular weight of from about 2500 to 50,000.

5. The pharmaceutical formulation according to claim 1 wherein the surfactant is a polyoxyethylene castor oil derivative with an HLB value of about 11 to 16.

6. The pharmaceutical formulation according to claim 1 wherein the potassium salt generating species is potassium hydroxide.

7. A process for preparing a dexibuprofen-containing soft gelatin capsule, comprising the steps of:

mixing dexibuprofen with a solubilizer, a surfactant, a co-surfactant, a potassium salt generating species, and a viscosity imparter to obtain a substantially clear dexibuprofen solution; and disposing the solution into a soft gelatin capsule.

8. The process of claim 7 wherein the solubilizer is diethylene glycol monoethylether;

the surfactant is selected from the group consisting of caprylocaproyl macrogol glycerides and polyoxyethylene castor oil derivatives;

the potassium salt generating species is potassium hydroxide; and the viscosity imparter is polyvinylpyrrolidone.

* * * * *